United States Patent [19]

Farrar, Jr. et al.

[11] Patent Number: 5,078,695
[45] Date of Patent: Jan. 7, 1992

[54] HOLDER FOR SYRINGE NEEDLE CAP

[76] Inventors: Robert J. Farrar, Jr., 138 Connie Dr., Pittsburgh, Pa. 15241; Michael Berry, R.D. 4, Box 23, Ligonier, Pa. 15658

[21] Appl. No.: 522,721

[22] Filed: May 14, 1990

[51] Int. Cl.$^5$ .......................................... A61M 58/32
[52] U.S. Cl. ................................ 604/192; 604/263; 128/919; 206/365
[58] Field of Search ............... 604/192, 263, 110, 187; 128/919; 206/365, 366

[56] References Cited

U.S. PATENT DOCUMENTS

| 4,485,918 | 12/1984 | Mayer | 206/366 |
|---|---|---|---|
| 4,623,336 | 11/1986 | Pedicano | 604/192 |
| 4,717,386 | 1/1988 | Simmons | 604/192 |
| 4,737,149 | 4/1988 | Gillilan | 604/192 |
| 4,846,803 | 7/1989 | Emerson | 604/263 |
| 4,915,698 | 4/1990 | Levenson | 604/192 |
| 4,938,354 | 7/1990 | Hernandez | 206/365 |
| 4,938,514 | 7/1990 | D'Addezio | 294/16 |
| 4,956,907 | 9/1990 | Bruno | 29/426.5 |
| 4,979,945 | 12/1990 | Wade et al. | 604/192 |
| 4,981,476 | 1/1991 | Aichlmayr et al. | 604/192 |

FOREIGN PATENT DOCUMENTS

| 2617719 | 1/1989 | France | 604/192 |
|---|---|---|---|
| 2198644 | 6/1988 | United Kingdom | 604/192 |
| 2209470 | 5/1989 | United Kingdom | 604/192 |

Primary Examiner—John D. Yasko
Assistant Examiner—Mark O. Polutta
Attorney, Agent, or Firm—William J. Ruano

[57] ABSTRACT

A needle cap holder of a syringe. It is of compressible material, such as rubber, having a central portion tapered inwardly from the top and bottom. It has a central, vertical cylindrical opening for receiving a needle cap of the syringe. It has a concave bottom portion.

1 Claim, 1 Drawing Sheet

HOLDER FOR SYRINGE NEEDLE CAP

This invention relates to a holder for a needle cap of a syringe to prevent unintentional autoinnoculation.

BACKGROUND OF THE INVENTION

Many infectious diseases are transmittable through unintentional needle pricks by misalignment of a syringe needle when returning it to a protective sheath.

SUMMARY OF THE INVENTION

The purpose of this invention is to provide a holder for the needle sheath so that the needle sheath does not have to be handled when resheathing the needle. The holder can be set or attached by various means, i.e. suction cup, velcro, specialized holder, to any surface. The invention relates to a compressible holder for a syringe needle cap, which holder is made of rubber, plastic, or other compressible material and has an opening centrally thereof to receive the sheath (cap). The holder may then be grasped to firmly hold the cap and protect the grasping hand while unsheathing. The sheath holder is self-supported in a position which the needle can be reinserted into the sheath contained within the sheath holder.

DESCRIPTION OF THE PREFERRED EMBODIMENT

Figure 1:
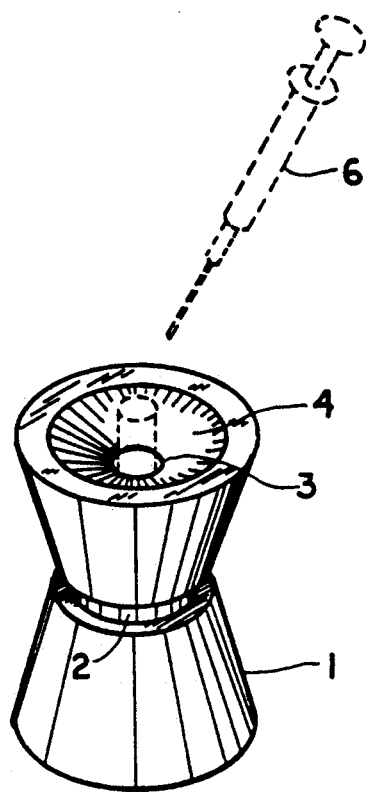
FIG. 1 is a top perspective view of a holder for the cap of a syringe embodying the present invention wherein the dash outline centrally thereof indicates a needle cap holder of a syringe shown separately in dotted outline and forming no part of the invention.
Figure 2:
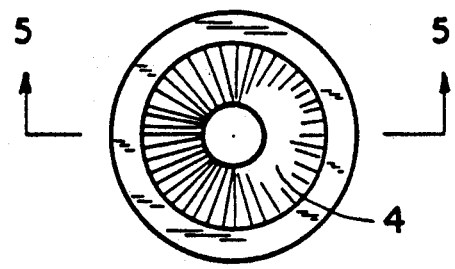
FIG. 2 is a top view of the holder.
Figure 4:
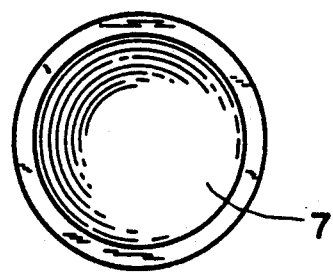
FIG. 4 is a bottom view thereof taken along line 4—4 of FIG. 3.
Figure 3:
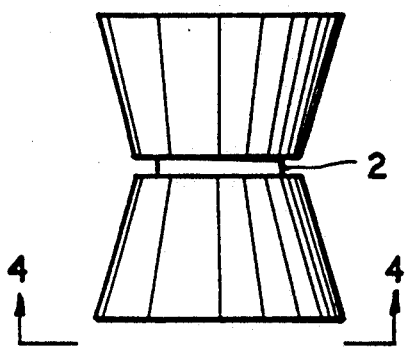
FIG. 3 is an elevational view thereof.
Figure 5:
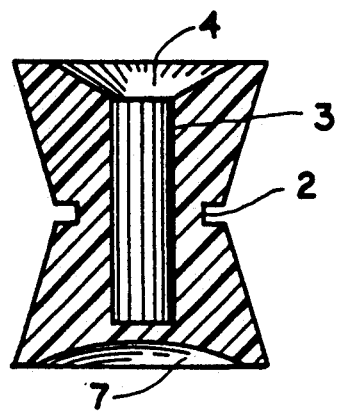
FIG. 5 is a vertical cross-sectional view thereof taken along line 5—5 of FIG. 2.

Referring to FIG. 1 of the drawing, numeral 1 denotes a needle cap holder of rubber, such as sponge rubber, or other compressible material and which has a top portion which is tapered inwardly, centrally thereof, either with or without a circular slot 2. The holder is tapered toward the center. A vertical cylindrical opening 3 is provided, centrally of the holder as best shown in FIG. 5, for receiving a needle cap, shown in dotted outline in FIG. 1. A cone shaped top portion or frustrum 4 is provided which may be coated or covered with a plastic protective covering (not shown), if desired.

In operation, the nurse or other medical personnel, will grasp and squeeze the central portion or slot 2 of the holder when the needle cap is in place, as shown in dotted outline, to insure a secure hold on the cap, particularly when the needle is projected therein or removed therefrom to the position shown at 6, that is away from the holder.

When it is desired to insert the needle into the cap, the holder 1 may be firmly secured to a table surface by pushing down and expelling air from the bottom concave surface 7, shown in FIG. 5. Thus the holder is not hand held while resheathing the needle. If the holder is alternatively hand held, the hand may be protected by virtue of the outward flare of the top portion of the holder.

Thus it will be seen that there is practically no danger of pricking the hand by the needle when it is pushed into or withdrawn from the needle cap as otherwise might occur.

While we have illustrated and described a single specific embodiment of our invention, it will be understood that this is by way of illustration only and that various changes and modifications may be contemplated in our invention within the scope of the following claims.

We claim:

1. A needle cap holder for syringe, said holder being circular and of rubber, having a top and bottom connected by side-walls and having a central vertical cylindrical opening for receiving a needle cap of the syringe, said holder being tapered inwardly on the side walls from the top and bottom to form two frustrums, a circular slot between said fustrums in concentric relationship with said vertical cylindrical opening to insure a secure hold on the cap, particularly when a needle is projected in said central vertical opening or removed therefrom, said holder having a concave top surface, said holder also having a concave bottom surface to serve as a suction cup for firmly holding the holder on a supporting surface.

* * * * *